United States Patent

Steele

(10) Patent No.: US 9,759,664 B2
(45) Date of Patent: Sep. 12, 2017

(54) MICROGRAVITY-COMPATIBLE ANALYSIS

(71) Applicant: Hamilton Sundstrand Space Systems International, Inc., Windsor Locks, CT (US)

(72) Inventor: John W. Steele, New Hartford, CT (US)

(73) Assignee: HAMILTON SUNDSTRAND SPACE SYSTEMS INTERNATIONAL, INC., Windsor Locks, CT (US)

( * ) Notice: Subject to any disclaimer, the term of this patent is extended or adjusted under 35 U.S.C. 154(b) by 77 days.

(21) Appl. No.: 14/724,361

(22) Filed: May 28, 2015

(65) Prior Publication Data

US 2016/0349184 A1   Dec. 1, 2016

(51) Int. Cl.

| G01N 21/78 | (2006.01) |
|---|---|
| G01N 33/18 | (2006.01) |
| G01N 31/22 | (2006.01) |
| G01N 21/75 | (2006.01) |
| G01N 21/77 | (2006.01) |

(52) U.S. Cl.
CPC .......... *G01N 21/78* (2013.01); *G01N 31/22* (2013.01); *G01N 33/18* (2013.01); *G01N 2021/757* (2013.01); *G01N 2021/7763* (2013.01)

(58) Field of Classification Search
CPC .. G01N 33/18; G01N 33/1813; G01N 33/182; G01N 33/20; G01N 31/22; G01N 21/77; G01N 21/78; G01N 2021/757; G01N 2021/7763; Y10T 436/175383; Y10T 436/19; Y10T 436/193333; Y10T 436/200833; Y10T 436/255; Y10T 436/2575

USPC ... 436/72, 84, 113, 124, 125, 128, 164, 165, 436/169, 178, 180; 422/400, 401, 420, 422/68.1, 534, 535, 554

See application file for complete search history.

(56) References Cited

U.S. PATENT DOCUMENTS

| 3,015,544 A | 1/1962 | Schneider, Jr. |
| 4,333,908 A | 6/1982 | Maki |
| 7,381,564 B2 | 6/2008 | Matschenko |
| 2004/0191119 A1* | 9/2004 | Zanzucchi ............. A61B 5/151 422/504 |
| 2006/0084176 A1 | 4/2006 | Almog |
| 2006/0084178 A1 | 4/2006 | Peyton |

OTHER PUBLICATIONS

Fritz et al. Journal of Chromatography A, vol. 997, 2003, pp. 41-50.*
Arena et al. Analytical Chemistry, vol. 74, 2002, pp. 185-190.*
Porter, Marc D. Abstract from Abstracts of Papers, 242$^{nd}$ ACS National Meeting & Exposition, Denver, CO, United States, Aug. 28-Sep. 1, 2011.*

* cited by examiner

Primary Examiner — Maureen Wallenhorst
(74) Attorney, Agent, or Firm — Cantor Colburn LLP

(57) ABSTRACT

A method of analyzing for the presence or concentration of an analyte in a liquid in microgravity is disclosed. The method includes removing a first quantity of the liquid from a first container and passing the removed liquid through a porous pad that includes a reagent that is responsive to the analyte. The presence or concentration of the analyte in the liquid is determined based on a response of the reagent. The removed quantity of liquid is transferred back to the first container or to a second container, and followed by disposal of the first or second container.

20 Claims, 1 Drawing Sheet

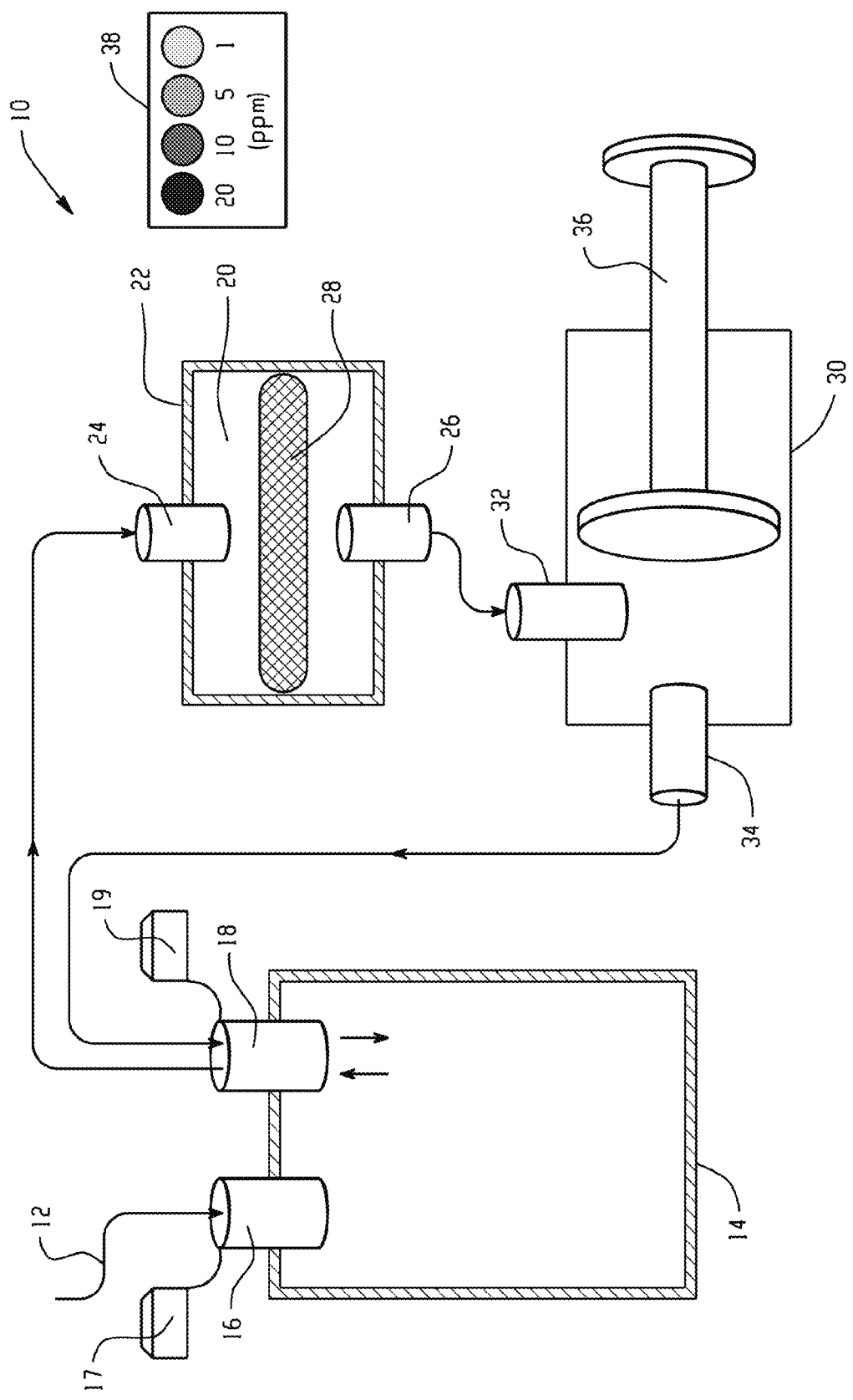

MICROGRAVITY-COMPATIBLE ANALYSIS

BACKGROUND

Through the many years of manned exploration of outer space, the composition and properties of water and other on-board liquids have typically been subject to a monitoring protocol that includes only periodic monitoring for some tests, and lack of monitoring at all for some components. Of course, water and other liquid management systems on board spacecraft tend to be robust, so it has typically been practiced that, absent outward signs of malfunction, testing for contaminants or properties that are out of specification has been thought to be necessary only periodically. This has meant that for short duration flights, no on-board monitoring is typically used. For long duration flights in Earth orbit, the periodic monitoring can be accomplished with samples being collected on-board and sent back to Earth for testing.

Notwithstanding the robustness of on-board water or other liquid management systems, there can be components in water or other liquids that can have a profound effect on personnel or on-board systems so that more frequent on-board monitoring is needed. This was demonstrated recently when silica buildup on spacesuit water separators caused a buildup of water inside the suit, necessitating an emergency abort of an astronaut spacewalk on the International Space Station. Additionally, the prospect of manned exploration of deep space will preclude the use of terrestrial testing, again necessitating that testing be conducted on-board.

BRIEF DESCRIPTION

In some aspects of this disclosure, a method of analyzing for the presence or concentration of an analyte in a liquid in microgravity comprises removing a first quantity of the liquid from a first container and passing the removed liquid through a porous pad comprising a reagent that is responsive to the analyte. The presence or concentration of the analyte in the liquid is determined based on a response of the reagent. The removed quantity of liquid is transferred back to the first container or to a second container, and followed by disposal of the first or second container.

In some aspects of this disclosure, a system for analyzing for the presence or concentration of an analyte in a liquid from a liquid source in microgravity includes a sealed sample collection container that includes a first port adapted for connection to the liquid source. The system also includes a test cassette comprising a sealed housing that includes an inlet port and an outlet port. The test cassette also includes a porous pad within the sealed housing comprising a reagent that is responsive to the analyte. The cassette is also configured to provide a flow of liquid from the inlet port through the porous pad to the outlet port. The system also includes a pump configured to transfer liquid from the sample collection container to the cassette inlet through the porous pad to the cassette inlet, and to the sample collection container or a second container.

In some aspects of this disclosure, a method of analyzing for the presence or concentration of an analyte in a liquid comprises passing a first quantity of the liquid through a porous pad comprising a reagent that is responsive to the analyte, and determining the presence or concentration of the analyte in the liquid based on a response of the reagent to the first quantity of liquid. If the first quantity of the liquid does not produce a measurable response by the reagent, an additional quantity or multiple quantities of the liquid are passed through the porous pad until the reagent produces a measurable response or a null response is noted.

BRIEF DESCRIPTION OF THE DRAWINGS

The subject matter that is regarded as the present disclosure is particularly pointed out and distinctly claimed in the claims at the conclusion of the specification. The foregoing and other features, and advantages of the present disclosure are apparent from the following detailed description taken in conjunction with the accompanying drawings in which:

The FIGURE is a schematic depiction of an exemplary system according to this disclosure.

DETAILED DESCRIPTION

Referring now to the FIGURE, an exemplary system 10 and process for testing a liquid such as water is depicted and described further below. As schematically depicted in the FIGURE, water 12 from a water source (not shown) is transferred into a first container 14 for testing. The container 14 can be any sort of container, although a polytetrafluoroethylene bag can be conveniently used and is very clean and impermeable. The container can include any sort of opening port/closure and fitting, and container 14 is depicted with a first female luer lock fitting 16 with tethered cap 17 for connecting to the water source, and a second female luer lock fitting 18 with tethered cap 19 for drawing and returning test samples. A test sample of a first quantity of the liquid is drawn from the container 14 and passed through a test cassette 20. Test cassette 20 has a sealed housing 22 with an inlet port 24 and outlet port 26. A test pad 28 is disposed within the sealed housing. Test pad 28 is a porous pad comprising a reagent that is responsive to the analyte being tested for.

The liquid is tested by passing it through the test pad 28. With continued reference to the FIGURE, the test cassette inlet port 24 is connected, either directly or with a connector, to the fitting 18 on container 14. A sampling syringe (i.e., pump) 30 has a one-way inlet valve 32, a one-way outlet valve 34, and a plunger 36. The sampling syringe inlet valve 32 is connected to the test cassette outlet port, and an outward stroke of the plunger 36 is used to draw liquid from the container 14, through the test cassette 20 and test pad 28, into the syringe 30. The test pad 28 can then be examined for a response such as a colorimetric response that can be compared to a reference chart 38. If the test cassette housing 22 is opaque, inspection of the test pad 28 would require disassembly of the cassette or opening of a viewing hatch. Alternatively, test cassette housing 22 can be transparent or can contain a transparent viewing window for the test pad 28.

An inward stroke of the plunger 36 will eject the test quantity of liquid from the syringe through one-way outlet valve 34. As depicted in the FIGURE, the syringe outlet valve 34 is connected to the second fitting 18 on container 14 to return the liquid to container 14 for disposal after a single-pass test by test pad 28. In some embodiments, however, a method is contemplated where additional quantities of test liquid are passed through test pad 28 to test for smaller quantities of the analyte. Some test protocols may be tolerant of re-use of the test liquid without significantly impacting the results. However for test protocols that require unadulterated liquid samples for testing, the syringe outlet valve 34 can be connected to a second (disposal) container (not shown) so that additional unadulterated samples of liquid can be drawn from container 14 for testing.

Varying the quantity of water passed through the test pad 28 can be used to expand the sensitivity of the test method. This can be accomplished if the reagent/analyte reaction is such that the response is proportional to the quantity of analyte that has reacted with the reagent. In this case, when the concentration of the analyte in the liquid is below the calibration threshold of the test pad so that no observable response is produced by the first quantity of liquid contacting the test pad, additional quantities of liquid can be passed through the test pad to increase the quantity of analyte that has reacted with the reagent. Such additional quantities can be repeated multiple times with intervening observations of the test pad until an observable result is produced or a null result (i.e., a determination that the level is effectively zero or below a level of concern). In such a case, the reference chart 38 can have multiple rows of numbers below each colorimetric sample, with each row corresponding to a concentrations represented by the reference circles for different total quantities of liquid passed through the test pad 28.

It should be noted that the system depicted in the FIGURE is exemplary in nature and should not be viewed as limiting. For example, embodiments are contemplated where test cassette 20 could be connected directly to a water source (first container) that is pressurized by a pump, and pressurized water then transferred through the cassette 20 to a second (disposal container) through a control valve that is used to control the quantity of liquid passed through the test pad 28.

Various types of materials can be used for the porous pad used to make test pad 28, including polymers such as polyether sulfone, cellulose acetate, mixed cellulose esters (MCE), polyethylene (PE), polyethylene/polyester (PE/PET), and styrene-based polymers, or inorganic materials such as porous ceramics. Various reagents can also be used as well, depending on the analyte being tested for. For example, one analyte of interest is silica, and exemplary reagents to test for silica can be selected according to the molybdosilicate method of the Standard Method 4500-SiO2 Silica (Editorial Revisions 2011) of the Standard Methods for the Examination of Water and Wastewater. Examples of such reagents include ammonium molybdate and oxalic acid. Other analytes can also be tested for, including but not limited to nickel, iron, ammonia, orthophthalaldehyde, dimethylsilanediol (DMSD), and iodine, as well as more mundane analytes such as ionic species associated with pH. Reagents to test for such analytes are known to those skilled in the art. The liquid being tested can comprise water (e.g., potable water, service water, ethylene glycol/water blends, or water-based borate/carbonate buffers), or non-aqueous liquids such as fluorocarbon refrigerants.

While the present disclosure provides detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various details of embodiments have been described, it is to be understood that some embodiments may include only some of these details. Accordingly, the present disclosure is not to be seen as limited by the foregoing description, but is only limited by the scope of the appended claims.

The invention claimed is:

1. A method of analyzing for the presence or concentration of an analyte in a liquid in microgravity, comprising transferring a first quantity of the liquid from a first container through a porous pad comprising a reagent that is responsive to the analyte, said porous pad disposed in a test cassette comprising a housing that includes an inlet port, an outlet port, and the porous pad within the housing between the inlet port and the outlet port, on a connected flow path from the first container, to the test cassette, to a pump, and to the first container or a second container;

determining the presence or concentration of the analyte in the liquid based on a response of the reagent; and disposing of the first or second container.

2. The method of claim 1, wherein the pump comprises a syringe comprising a syringe body, a plunger, and an inlet port, and the first quantity of the liquid is removed from the first container by actuating the plunger with a first stroke to draw liquid into the syringe through the inlet port.

3. The method of claim 2, wherein the syringe further comprises an outlet port, and the removed liquid is transferred to the first or second container by actuating the plunger with a second stroke to expel liquid from the outlet port.

4. The method of claim 3, wherein the inlet port and outlet port each include a one-way valve.

5. The method of claim 1, wherein the first quantity of liquid is transferred from the pump to the first container.

6. The method of claim 1, further comprising, if the reagent does not produce a measurable response after passing the first quantity of liquid through the porous pad, passing additional quantity or quantities of the liquid through the porous pad until the reagent produces a measurable response.

7. The method of claim 6, further comprising determining a concentration of the analyte in the liquid based on the response produced by the reagent and a total quantity of liquid passed through the porous pad.

8. The method of claim 6, wherein the first quantity of liquid and the additional quantity or quantities of removed liquid are transferred from the pump to a second container.

9. The method of claim 1, further comprising transferring liquid from a stationary liquid source to the first container, and transporting the first container to a location remote from the stationary liquid source before removing the first quantity of liquid from the first container.

10. The method of claim 1, wherein the liquid is water, and the reagent and analyte react to produce a colorimetric response.

11. The method of claim 10, wherein the analyte is selected from the group consisting of silica, nickel, iron, ammonia, orthophthalaldehyde, and iodine.

12. The method of claim 10, wherein the analyte is silica.

13. A system for analyzing for the presence or concentration of an analyte in a liquid from a liquid source, comprising system components disposed in a microgravity environment, said system components comprising:

a sealed sample collection container that includes a first port connection to the liquid source;

a test cassette comprising a sealed housing that includes an inlet port and an outlet port, and a porous pad within the sealed housing comprising a reagent that is responsive to the analyte, the cassette configured to provide a flow of liquid from the inlet port through the porous pad to the outlet port; and a pump configured to transfer liquid along a connected flow path from the sample collection container through the cassette inlet, the porous pad, the cassette outlet, the pump, and to the sample collection container or a second container.

14. The system according to claim 13, wherein the sealed sample collection container further includes a second port connection to the test cassette or the pump.

15. The system according to claim 13, wherein the pump is a syringe comprising a syringe body, a plunger, an inlet, and an outlet, the syringe configured to draw liquid into the syringe body through the syringe inlet by actuating the plunger with a first stroke, and to expel liquid from the syringe body through the syringe outlet by actuating the plunger with a second stroke.

16. The system of claim 13, further comprising a color reference chart for correlating a colorimetric response from the reagent exposed to the analyte to a concentration of the analyte in the liquid.

17. The system of claim 16, wherein each color on the reference chart correlates to more than one concentration value, based on different quantities of liquid passed through the porous pad.

18. The system of claim 13, wherein the liquid comprises water, and the reagent and analyte react to produce a colorimetric response.

19. The system of claim 18, wherein the analyte is selected from the group consisting of silica, nickel, iron, ammonia, orthophthalaldehyde, dimethylsilanediol (DMSD), and iodine.

20. A method of analyzing for the presence or concentration of an analyte in a liquid, comprising
  passing a first quantity of the liquid through a porous pad comprising a reagent that is responsive to the analyte;
  determining the presence or concentration of the analyte in the liquid based on a response of the reagent to the first quantity of liquid;
  if the first quantity of the liquid does not produce a measurable response by the reagent, passing additional quantity or quantities of the liquid through the porous pad until the reagent produces a measurable response; and
  determining a concentration of the analyte in the liquid based on the response produced by the reagent and a total quantity of liquid passed through the porous pad.

* * * * *